United States Patent
Han et al.

(10) Patent No.: US 10,126,285 B2
(45) Date of Patent: Nov. 13, 2018

(54) APPARATUS AND METHOD FOR PREDICTING SLAB QUALITY

(71) Applicant: POSCO, Pohang-Si (KR)

(72) Inventors: Sang Woo Han, Pohang-Si (KR); Yong Jin Kim, Gwangyang-Si (KR); Joong Kil Park, Pohang-Si (KR); Sung Kwang Kim, Gwangyang-Si (KR)

(73) Assignee: POSCO, Pohang-Si (KR)

( * ) Notice: Subject to any disclaimer, the term of this patent is extended or adjusted under 35 U.S.C. 154(b) by 836 days.

(21) Appl. No.: 14/416,429

(22) PCT Filed: Dec. 28, 2012

(86) PCT No.: PCT/KR2012/011718
§ 371 (c)(1),
(2) Date: Jan. 22, 2015

(87) PCT Pub. No.: WO2014/017714
PCT Pub. Date: Jan. 30, 2014

(65) Prior Publication Data
US 2015/0204837 A1    Jul. 23, 2015

(30) Foreign Application Priority Data

Jul. 24, 2012 (KR) .................. 10-2012-0080436

(51) Int. Cl.
G01N 33/20 (2006.01)
B22D 11/16 (2006.01)
B22D 11/20 (2006.01)

(52) U.S. Cl.
CPC ........... *G01N 33/206* (2013.01); *B22D 11/16* (2013.01); *B22D 11/201* (2013.01)

(58) Field of Classification Search
CPC ..... B22D 11/16; B22D 11/201; G01N 33/206
See application file for complete search history.

(56) References Cited

U.S. PATENT DOCUMENTS

| | | | |
|---|---|---|---|
| 5,020,585 A | 6/1991 | Blazek et al. | |
| 5,884,685 A | 3/1999 | Umezawa et al. | |

(Continued)

FOREIGN PATENT DOCUMENTS

| | | |
|---|---|---|
| CN | 1045720 A | 10/1990 |
| CN | 1152267 A | 6/1997 |

(Continued)

OTHER PUBLICATIONS

Thomas, Brian G., "Modeling of Continuous Casting Defects Related to Mold Fluid Flow", Jul. 2006, AIST Iron & Steel Technology, vol. 3, No. 5, pp. 2-17.*

(Continued)

*Primary Examiner* — Mischita Henson
(74) *Attorney, Agent, or Firm* — The Webb Law Firm (57) ABSTRACT

Provided are an apparatus and method for predicting slab quality including a plurality of meniscus height detecting units prepared in a plurality of region on a top side of a mold receiving molten steel, and detecting a meniscus height of the molten steel, a meniscus flow detecting unit creating a meniscus flow pattern using meniscus heights at the plurality of regions, which are detected by the plurality of meniscus height detecting units, a data storage unit storing the meniscus flow pattern and quality data of a slab produced accordingly and a slab quality predicting unit extracting the meniscus flow pattern detected by the meniscus flow detecting unit and consequent slab quality from the data storage unit to predict slab quality.

12 Claims, 9 Drawing Sheets

(56) References Cited

U.S. PATENT DOCUMENTS

| | | | |
|---|---|---|---|
| 6,024,161 A | 2/2000 | Fujioka et al. | |
| 2011/0144926 A1 | 6/2011 | Lieftucht et al. | |
| 2013/0333473 A1* | 12/2013 | Cestari | B22D 2/00 73/584 |

FOREIGN PATENT DOCUMENTS

| | | |
|---|---|---|
| CN | 101347822 A | 1/2009 |
| CN | 102089096 A | 6/2011 |
| CN | 102319883 A | 1/2012 |
| EP | 1166921 A1 | 1/2002 |
| JP | 58104929 U | 7/1983 |
| JP | 63212054 A | 9/1988 |
| JP | 03-060852 | 3/1991 |
| JP | 04-143056 | 5/1992 |
| JP | 5104221 A | 4/1993 |
| JP | 05-329604 | 12/1993 |
| JP | 10277706 A | 10/1998 |
| JP | 2002-206958 A | 7/2002 |
| JP | 2003-181609 | 7/2003 |
| JP | 2004-025202 A | 1/2004 |
| JP | 2004-066303 A | 3/2004 |
| JP | 2008221287 A | 9/2008 |
| JP | 2012-076094 A | 4/2012 |
| KR | 10-2000-0040915 A | 7/2000 |
| KR | 10-2001-0055792 A | 7/2001 |
| KR | 1020030053080 A | 6/2003 |
| KR | 10-2004-0038224 A | 5/2004 |
| KR | 10-0709000 B1 | 4/2007 |
| KR | 10-0801116 B1 | 1/2008 |
| KR | 10-2011-0034474 A | 4/2011 |
| KR | 10-2012-0032921 A | 4/2012 |
| KR | 10-2012-0032923 A | 4/2012 |
| KR | 10-2012-0044421 A | 5/2012 |
| KR | 10-2012-0044425 A | 5/2012 |
| KR | 10-2012-0444423 A | 5/2012 |
| KR | 10-2012-0057901 A | 6/2012 |
| WO | 96/30141 A1 | 10/1996 |

OTHER PUBLICATIONS

Thomas, B. G. et al, "Transient Fluid-Flow Phenomena in the Continuous Steel-Slab Casting Mold and Defect Formation", Dec. 2006, Journal of Metals electronic edition, pp. 1-20.*

Hardin, R. et al., "Three-dimensional Simulation of Heat Transfer and Stresses in a Steel Slab Caster", Jun. 27, 2011, Metec InSteelCon 2011, Session 2, pp. 1-6.*

Camisani-Calzolri, F.R. et al., "Defect and mould variable prediction in continuous casting", 20013, Application of Computers and Operations Research in the Minerals Industries, 99 253-260.*

Thomas, B. G., "On-line Detection of Quality Problems in Continuous Casting of Steel", Nov. 10, 2003, 2003 Materials Science & Technology Symposium, pp. 29-45.*

Hinterkoerner, R. et al., "Slab-Quality Prediction with In-Depth Metallurgical Modeling", Sep. 2004, la metallurgia italiana, pp. 55-59.*

Higson, S. R. et al., "Flowvis: measurement, prediction and control of steel flows in the casting nozzle and mould", 2010, European Commission Research Fund for Coal & Steel, EUR24205, pp. 1-103.*

Anagnostopoulos, J. et al., "Three-Dimensional Modeling of the Flow and the Interface Surface in a Continuous Casting Mold Model", Dec. 1999, Metallurgigal and Materials Transactions, vol. 30B, pp. 1095-1105.*

* cited by examiner

APPARATUS AND METHOD FOR PREDICTING SLAB QUALITY

CROSS-REFERENCE TO RELATED APPLICATIONS

This application is the United States national phase of International Application No. PCT/KR2012/011718 filed Dec. 28, 2012, and claims priority to Korean Patent Application No. 10-2012-0080436 filed Jul. 24, 2012, the disclosures of which are hereby incorporated in their entirety by reference.

TECHNICAL FIELD

The present invention relates to an apparatus for predicting slab quality, and more particularly to an apparatus and method for predicting slab quality capable of visualizing a flow of meniscus to a user and predicting slab quality using a pattern according to the flow of meniscus.

BACKGROUND ART

Typically, a continuous casting process is a process of continuously pouring molten steel into a mold having a certain shape, continuously drawing semi-solidified molten steel in the mold towards the bottom side, and manufacturing a semi-finished product having various shapes such as a slab, a bloom, or a billet. The mold has cooling water circulated therein to semi-solidify the poured molten steel and make a certain form. In other words, the molten steel in a molten state is semi-solidified by a cooling action in the mold, non-solidified molten steel drawn from the mold is solidified by air mist in which air and cooling water sprayed from a slab cooling system are mixed to form a slab in a perfect solid state.

Primary cooling in the mold is the most important process for determining slab surface quality. In other words, the primary cooling depends on the molten steel flow in the mold. When a rapid flow or a bias flow occurs in the meniscus, a mold flux playing a role of lubricant and heat reserving is caused and accordingly defects occur on the slab.

Accordingly, once the flow of meniscus is measured, slab defects may be predicted. However, since meniscus maintains a high temperature state, it is very difficult to measure a flow thereof in real time. In addition, even though a technique for measuring the height of the meniscus using an eddy current level meter to control a uniform height of the molten steel in the mold is commercially available, since the height of only any one point is measured, it is not possible to measure the molten steel flow of the entire meniscus. In addition, since a mold flux is coated on the meniscus for reserving heat of the meniscus, naked eye observation using a camera or the like is not possible.

Of background interest is Korean patent laid-open publication No. 2001-0055792.

The present invention provides an apparatus and method for predicting slab quality capable of visualizing a meniscus flow to a user and predicting quality such as presence or not of slab defects using a pattern according to a meniscus flow type.

The present invention also provides an apparatus and method for predicting slab quality capable of measuring a meniscus flow in real time by preparing a plurality of meniscus height detecting units including temperature detecting means on the mold and detecting the height of the meniscus using the prepared meniscus height detecting unit.

The present invention also provides an apparatus and method for predicting slab quality capable of storing a meniscus flow pattern and quality of a slab produced accordingly as data, and predicting the slab quality according to the data stored according to the meniscus flow pattern, which is measured in real time through a plurality of meniscus position detecting units.

SUMMARY OF THE INVENTION

In accordance with an exemplary embodiment of the present invention, an apparatus for predicting slab quality includes: a plurality of meniscus height detecting units prepared in a plurality of region on a top side of a mold receiving molten steel, and detecting a meniscus height of the molten steel; a meniscus flow detecting unit creating a meniscus flow pattern using meniscus heights at the plurality of regions, which are detected by the plurality of meniscus height detecting units; a data storage unit storing the meniscus flow pattern and quality data of a slab produced accordingly; and a slab quality predicting unit extracting the meniscus flow pattern detected by the meniscus flow detecting unit and consequent slab quality from the data storage unit to predict slab quality.

The apparatus may further include a display unit displaying the meniscus flow pattern and the consequent slab quality to a user.

The plurality of meniscus height detecting units may include at least any one selected from temperature detecting means, electromagnetic induction sensors, and radiation measuring means.

The temperature detecting means may be installed at an identical height on the top side of the mold.

The temperature detecting means may be installed at a height in a range of 4.5 mm to 9.5 mm from the meniscus.

The meniscus flow detecting unit may create a 3-dimensional (3D) meniscus flow image according to the meniscus heights and a 2-dimensional (2D) meniscus flow pattern from the 3D image.

The 3D meniscus flow image may be created using temperature differences between the plurality of regions measured through the temperature detecting means.

The 3D meniscus flow image may be created with a vertical distance between the temperature detecting means and the meniscus, which is calculated by applying the temperatures measured through the temperature detecting means to the following Equation (1), $$\alpha \times 2.5 \times Q = \left(\frac{K_{slag}}{d_{slag}} + \frac{K_{cu}}{d_{cu}}\right) \times (T_{steel} - T_1) \quad (1)$$

$$d_{cu} = \sqrt{d_1^2 + d_2^2}$$

where $\alpha$ denotes a correction coefficient using an eddy current sensor, Q denotes a real time heat flux using a temperature difference at an input/output side of the mold, $K_{slag}$ denotes a heat transfer coefficient of a slag, $K_{cu}$ denotes a heat transfer coefficient of the mold, $d_{slag}$ denotes the thickness of a slag layer, $d_{cu}$ denotes a diagonal distance between the molten steel contacting the short side of the mold and the thermocouple, $T_{steel}$ denotes a real time temperature of the molten steel, $T_1$ denotes a real time temperature of the thermocouple, $d_1$ denotes a vertical distance between the thermocouple and the meniscus, and $d_2$ denotes a distance between a side surface of the mold and a tip of the thermocouple.

After provision of the molten steel to the mold is completed, the meniscus flow pattern may be created at least once.

The data storage unit may perform matching of the meniscus flow pattern in plurality with at least one selected from presence or not of defects, defect positions, and defect shapes of the consequent slab in plurality and stores the matched results.

The display unit may display at least any one piece of information provided from the meniscus height detecting units, the meniscus flow detecting unit, the meniscus flow detecting unit, the data storage unit, and the slab quality predicting unit.

In accordance with another exemplary embodiment of the present invention, a method of predicting slab quality includes: installing a plurality of meniscus height detecting units at a plurality of regions of a mold; creating a meniscus flow pattern using the meniscus heights at the plurality of regions, which are detected by the plurality of meniscus height detecting units; comparing pre-stored meniscus flow pattern data with a current meniscus flow pattern in the mold; and extracting meniscus flow pattern data matched with the current meniscus flow pattern in the mold and consequent slab quality data to predict quality of a slab by the current meniscus flow pattern.

The method may further include storing a plurality of meniscus flow pattern data and a plurality of slab quality data accordingly produced.

The method may further include displaying the meniscus flow pattern and the consequent slab quality to a user.

The method of claim 13, further comprising, when the current meniscus flow pattern is not matched with the meniscus flow pattern data, making the current meniscus flow pattern and the consequent slab quality as data and storing the data.

The creating of the meniscus flow pattern may include creating a 3D meniscus flow image using the meniscus heights and creating a 2D meniscus flow pattern from the 3D image.

According to embodiments of the present invention, a plurality of meniscus height detecting units including a temperature detecting means are installed on a top side of a mold to detect the heights of meniscus at a plurality of regions, and visualize the detected heights as a meniscus flow pattern. In addition, slab quality including presence or not of slab defects according to the meniscus flow pattern is tracked and made as data. Furthermore, the meniscus flow pattern according to the meniscus height measured in real time is compared with the meniscus flow pattern made as data and the consequent slab quality, and then presence or not of slab defects is displayed to a user.

According to embodiments of the present invention, a meniscus flow can be detected in real time by preparing a plurality of meniscus height detecting units at the top side of a mold. In addition, since presence or not of slab defects according to a meniscus flow pattern can be predicted, the slab defects can be prevented in advance. In other words, slab quality can be improved by controlling the meniscus flow pattern so as to prevent the slab defects from occurring.

MODE FOR CARRYING OUT THE INVENTION

Hereinafter, specific embodiments will be described in detail with reference to the accompanying drawings. The present invention may, however, be embodied in different forms and should not be construed as limited to the embodiments set forth herein. Rather, these embodiments are provided so that this disclosure will be thorough and complete, and will fully convey the scope of the present invention to those skilled in the art. Like reference numerals refer to like elements throughout.

Figure 1:
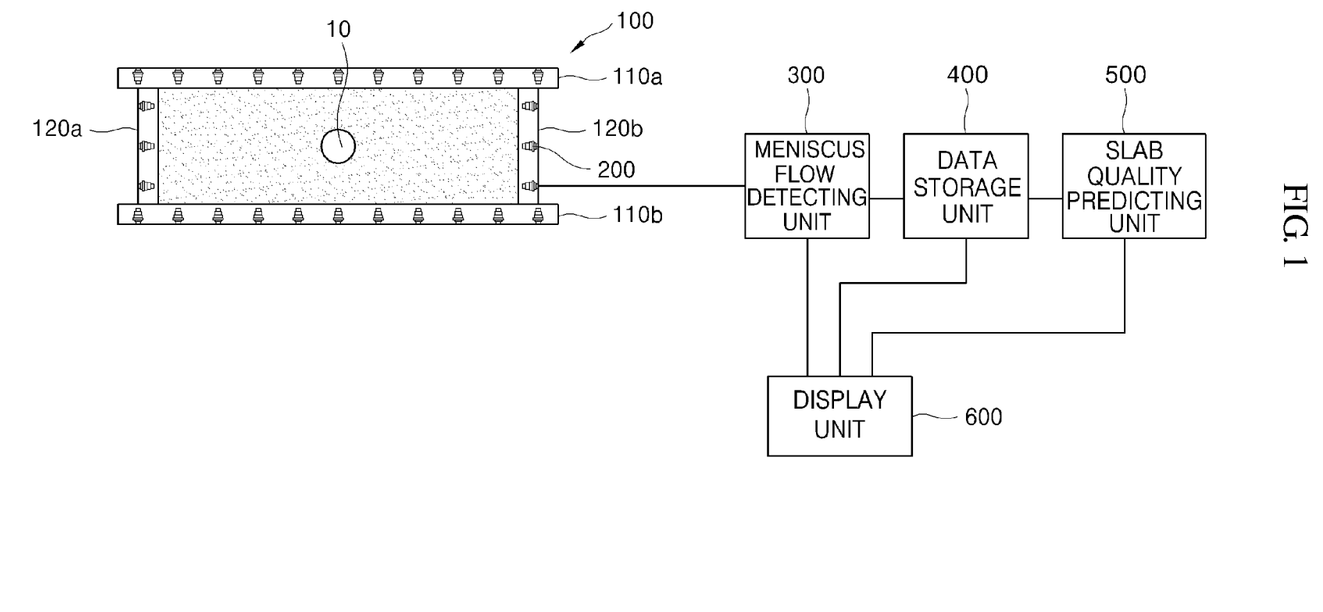
FIG. 1 is a configuration diagram of a slab quality predicting apparatus according to an embodiment of the present invention.
Figure 2:
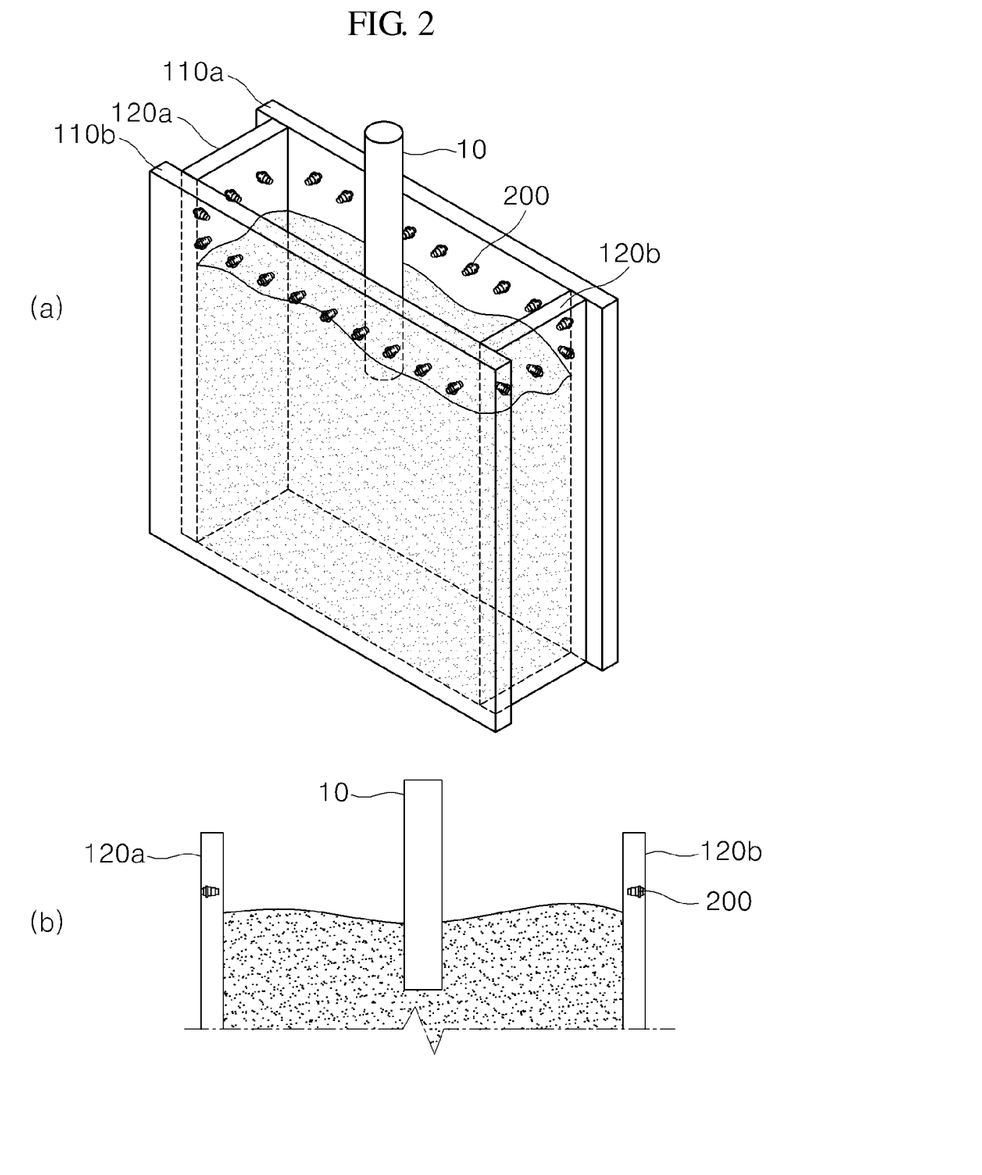
FIG. 2 is schematic diagrams of a mold of a slab quality predicting apparatus and a meniscus height detecting unit installed thereon according to an embodiment of the present invention.
Figure 3:
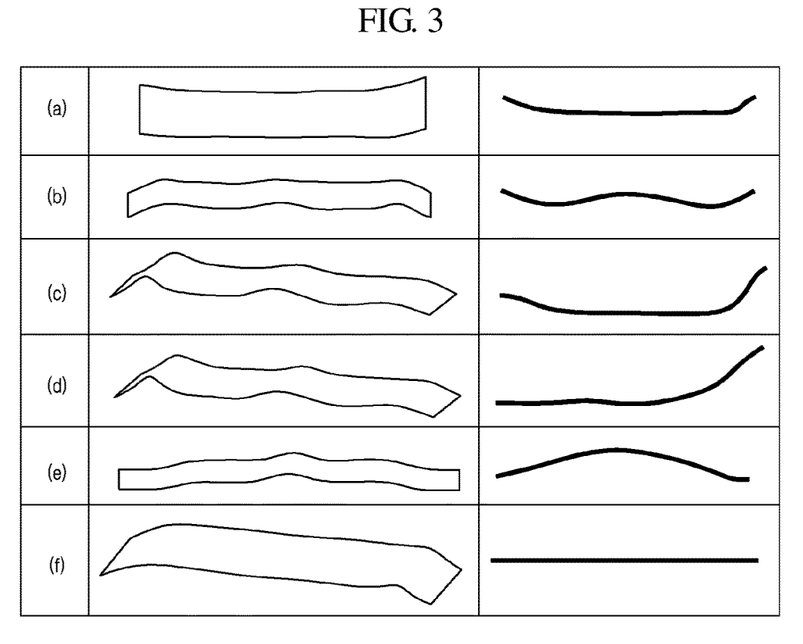
FIG. 3 shows meniscus flow patterns detected by a slab quality predicting apparatus according to an embodiment of the present invention.
Figure 4:
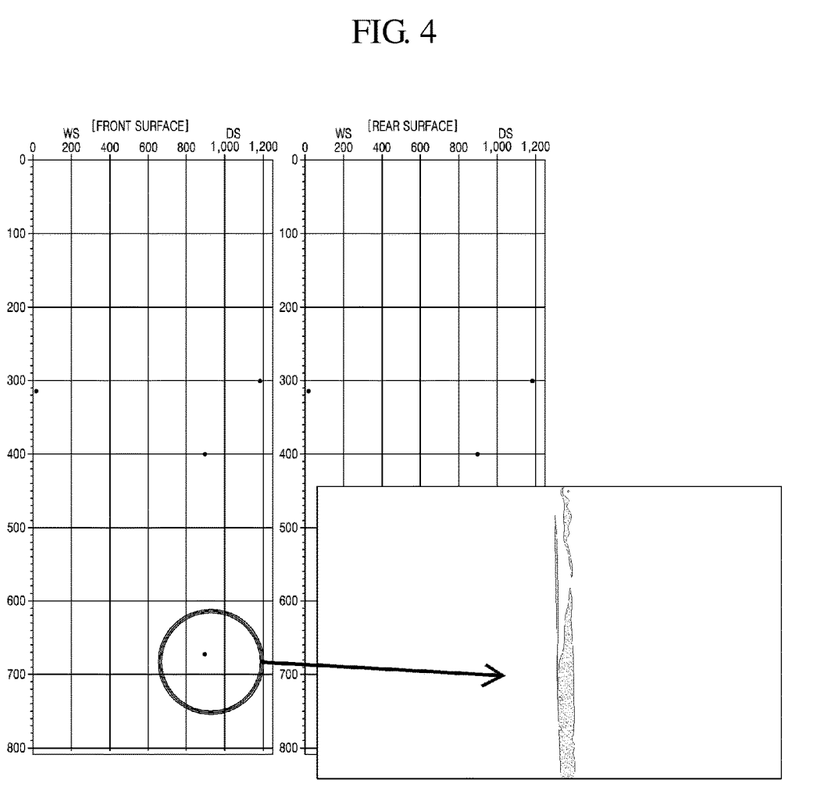
FIG. 4~6 illustrate defects of a slab produced according to the meniscus flow pattern.
Figure 5:
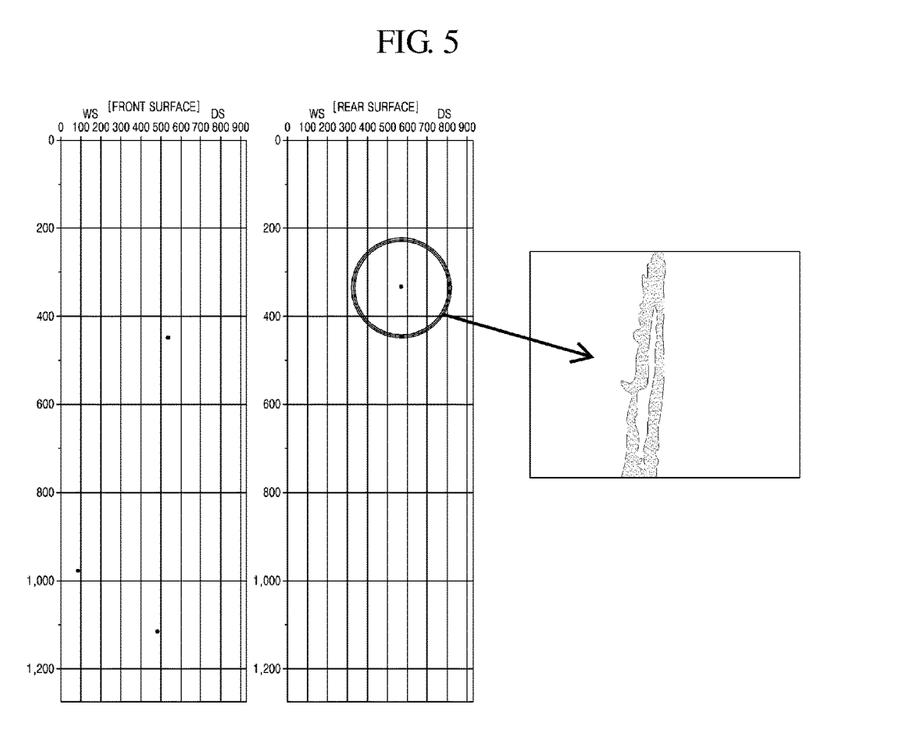
Figure 6:
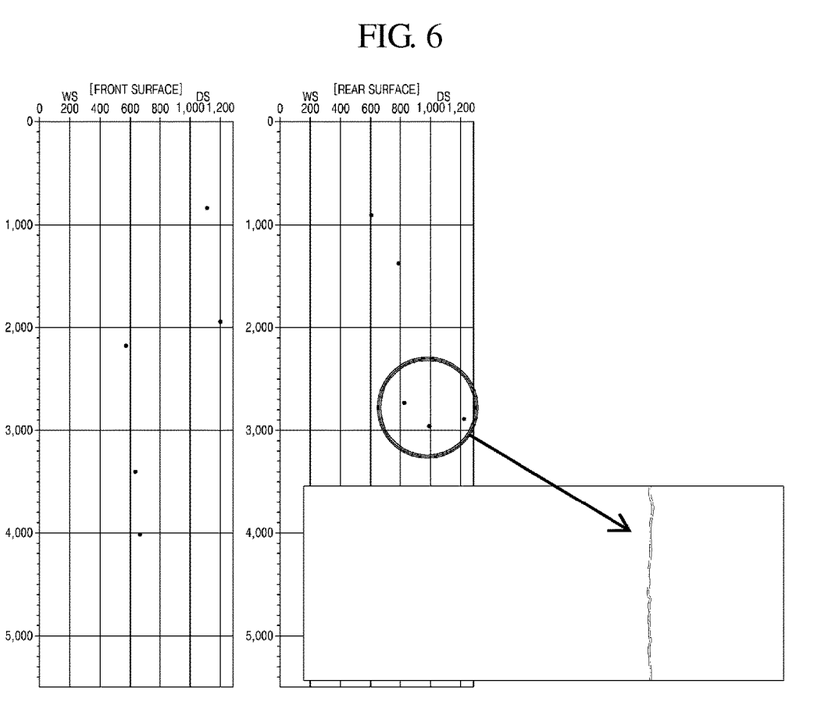
Figure 7:
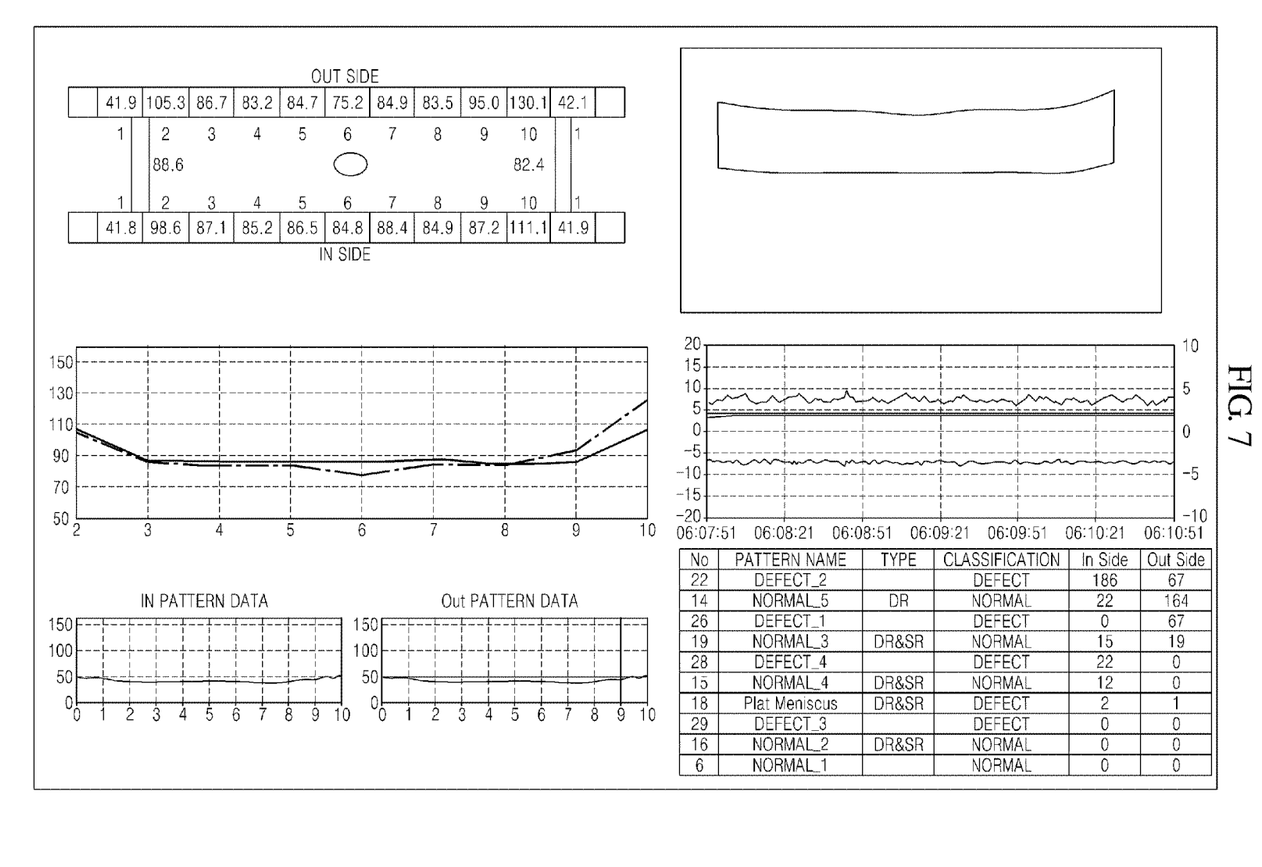
FIG. 7 illustrates an example displayed to a user.

FIG. 1 is a configuration diagram of a slab quality predicting apparatus according to an embodiment of the present invention, and FIG. 2 is schematic diagrams of a mold and a meniscus height detecting unit of the slab quality predicting apparatus. In addition, FIG. 3 shows 3-dimensional (3D) and 2-dimensional (2D) shapes of various meniscus flow patterns, and FIGS. 4~6 show views showing aspects of slab defects according to the meniscus flow pattern. In addition, FIG. 7 illustrates an example displayed to a user by a slab quality predicting apparatus according to an embodiment of the present invention.

Referring to FIG. 1, a slab quality predicting apparatus according to an embodiment of the present invention includes a mold 100 receiving molten steel from a submerged entry nozzle 10, a plurality of meniscus height detecting units 200 prepared at a plurality of regions and detecting heights of a meniscus at the plurality of regions, a meniscus flow detecting unit 300 creating a meniscus flow pattern using the heights of the meniscus detected at the plurality of regions by the plurality of meniscus height detecting units 200, a data storage unit 400 storing meniscus flow pattern data and slab quality data produced accordingly, a slab quality predicting unit 500 predicting slab quality by extracting the meniscus flow pattern detected by the meniscus flow detecting units 300 and the consequent slab quality from the data storage unit 400, and a display unit 600 displaying the meniscus flow pattern, the consequent slab defects and the like to the user.

The mold 100 receives the molten steel provided from the submerged entry nozzle 10 and primarily cools the molten steel to solidify the molten steel in a predetermined slab shape. Such a mold 100 includes, as illustrated in FIG. 2, two long sides 110a and 110b separated from each other by a predetermined distance to face each other, and two short sides 120a and 120b separated from each other by a predetermined distance between the two long sides 110 and 110b to face each other. Here, the long sides 110a and 110b, and the short sides 120a and 120b may be respectively manufactured with, for example, copper. Accordingly, the mold 100 has a predetermined space prepared to receive the molten steel between the two long sides 110a and 110b, and the two short sides 120*a* and 120*b*. In addition, the submerged entry nozzle 10 is prepared at a central part formed from the two long sides and the two short sides. The molten steel received from the submerged entry nozzle 10 is provided symmetrically from the central part of the mold 100 towards the outside direction and form a jet stream while showing a specific flow phenomenon according to a manufacturing condition and the like. Furthermore, the molten steel may be received in the mold 100 to allow the top end portion of the mold 100 to remain with a predetermined width and a mold flux may be coated on the molten steel. The surface of the molten steel becomes the meniscus.

The meniscus height detecting units 200 detect the heights of the meniscus at the plurality of regions on the meniscus in the mold 100. For example, the meniscus height detecting units 200 may measure a temperature at at least any one time using a temperature detecting means, and measure a temperature change of the meniscus by measuring the temperature in real time. To this end, the meniscus position detecting unit 200 may include a plurality of thermocouples prepared at a plurality of regions on the long sides 110*a* and 110*b* of the mold 100 and the short sides 120*a* and 120*b* of the mold 100 and measuring a temperature of the meniscus. In other words, the plurality of thermocouples may be prepared, as illustrated in FIG. 2, in a uniform interval at an identical height of the long sides 110*a* and 110*b* and the short sides 120*a* and 120*b* of the mold 100 and measure the temperature of the meniscus at each region. For example, the plurality of thermocouples may be installed in a uniform interval in a range of 110 mm to 150 mm at an identical height in a range of about −50 mm to +50 mm from the meniscus. In other words, the thermocouples may be installed at a position in a range from a height lower than the meniscus by 50 mm and to a height higher by 50 mm. However, at the time of continuous casting, the entire height of the meniscus is in a range of −2 mm to 3 mm around the submerged entry nozzle 10 and in a range of +2 mm to +4 mm around edges. In other words, the height of the meniscus may be lower than those of other portions around the submerged entry nozzle 10 and higher than those of other portions around the edges. Accordingly, an optimal thermocouple height for detecting the meniscus height is about 4.5 mm and a maximum height that the thermocouple may measure the meniscus flow may be 9.5 mm. If the height of thermocouple is lower than 4.5 mm, the thermocouple may be submerged in the meniscus according to the meniscus flow. In addition, if the height of the thermocouple is higher than 9.5 mm, the observation sensitivity of a meniscus behavior around the submerged entry nozzle 10 becomes degraded and a reaction speed difference between the thermocouples and a temperature difference between the thermocouples are small, and accordingly evaluation becomes difficult. Furthermore, since installed in the mold 100 to measure only the edge height of the meniscus, the thermocouple is difficult to measure the height of a middle point of the meniscus. However, the thermocouple enables cheap installment in plurality in terms of cost and precise measurement since the thermocouples measure the edge heights at a plurality of positions and image-processes the measured edge heights. In addition, in order to compensate for meniscus height measurement of the thermocouple, an electromagnetic induction sensor may be used interchangeably with the thermocouple. In other words, the electromagnetic induction sensor may be positioned at a central part of the meniscus and measure the entire height of the meniscus of the mold 100.

The meniscus flow detecting unit 300 creates a 3D image using a meniscus temperature of each region, which is measured by the meniscus height detecting units 200, for example, the plurality of thermocouples, and creates a 2D pattern from the 3D image. In other words, the meniscus flow detecting unit 300 creates a 3D meniscus shape using the meniscus temperatures measured by the plurality of thermocouples, displays the 3D meniscus shape to the user through the display unit 600, and derives a 2D meniscus flow pattern from the 3D meniscus shape to display the 2D meniscus flow pattern to the user through the display unit 600 and to simultaneously store in the data storage unit 400. For example, when the meniscus rises or falls due to fluctuation of the molten steel, the entire meniscus shape may be detected using a difference in temperature measured at each region and visualized in a 3D image and a 2D pattern. In other words, once the temperature of the thermocouple rises, the meniscus height is raised and the meniscus is close to the thermocouple. Once the temperature of the thermocouple falls, the meniscus height is lowered and the meniscus is far away from the thermocouple. Accordingly, the meniscus flow may be detected using a difference between temperatures measured by the plurality of thermocouples and the meniscus flow may be visualized in a 3D image and a 2D pattern. At this point, the meniscus flow detecting unit 300 may detect the meniscus flow according to the meniscus height at a predetermined time. For example, after a predetermined time from when provision of the molten steel from the submerged entry nozzle 10 is completed, the meniscus flow may be detected according to the temperatures measured by the plurality of thermocouples. In addition, the meniscus flow may be detected according to a time change with a predetermined time difference. As illustrated in FIG. 3, a plurality of meniscus images and flow patterns may be derived using meniscus temperatures measured by the plurality of thermocouples. In other words, in FIG. 3(*a*), two short side portions almost identically show a somewhat high temperature, and the other portions show a flow pattern that maintains almost identical temperature wherein the flow pattern is a very stable meniscus flow pattern in which a proper meniscus speed and temperature may be secured without a bias flow. A slab produced with such a flow pattern has very low possibility of defect occurrence. In addition, in FIG. 3(*b*), the two short side portions and the central part almost identically show a somewhat high temperature, the other portions show a flow pattern that maintains almost identical temperature wherein although being stable without bias flow occurrence, the flow pattern is a meniscus flow pattern in which argon (Ar) rises very weakly around the submerged entry nozzle. A slab produced with such a flow pattern has also very low possibility of defect occurrence. FIG. 3(*c*) shows a flow pattern that a temperature of any one short side portion is significantly higher than temperatures of the other portions, and FIG. 3(*d*) shows a flow pattern that a temperature of any one short side portion is lower than the case of FIG. 3(*c*) but higher than temperature of the other portions. Such a flow pattern occurs because a bias flow seriously appears due to blockage of the submerged entry nozzle 10 and a produced slab has very high possibility of defect occurrence due to creation of a vortex or the like. In addition, FIG. 3(*e*) shows a flow pattern in which a temperature gradually rises from the short side portion to the central part. Such a flow pattern is created by open-air inclusion, out-of-control of argon amount, submerged entry nozzle evaporation, or the like, and a defect is caused by inclusions attached around bubbles due to the open air having a lot of oxygen. FIG. 3(*f*) shows a meniscus flow pattern that maintains an almost identical temperature in the entire meniscus. Such a meniscus flow pattern is caused by a large temperature drop due to downflow occurrence or a low meniscus speed, and a slab has high possibility of hole type defect occurrence.

The data storage unit 400 stores meniscus flow patterns of various shapes, and observes and measures quality of a slab produced accordingly and stores data thereof. In other words, the data storage unit 400 makes various meniscus flow patterns detected and visualized by the meniscus flow detecting unit 300 as data and stores the data, and tracks slab quality such as presence or not of defects and defect positions in a slab produced with the various meniscus flow patterns and stores data thereof. In addition, the data storage unit 400 may store a cause of defect occurrence of a slab, namely, a cause of an abnormal meniscus flow pattern or the like. At this point, the meniscus flow pattern and consequent slab quality may be matched with a cause of defect occurrence and stored. For example, a slab produced with the meniscus flow pattern illustrated in FIGS. 3(*a*) and 3(*b*) may be determined as normal, since having a low possibility of defect occurrence. However, a slab produced with the meniscus flow pattern illustrated in FIGS. 3(*c*) and 3(*d*) has a high possibility of defect occurrence, since a vortex or the like is created in the front surface of the slab as illustrated in FIG. 4. In addition, a slab produced with the meniscus flow pattern illustrated in FIG. 3(*e*) has a high possibility of occurrence of a plurality of hole type defects, since inclusions are attached around bubbles by the open air having a lot of oxygen on the rear surface as well as the front surface of the slab, as illustrated on FIG. 5. In addition, a slab produced with the meniscus flow pattern illustrated in FIG. 3(*f*) has a high possibility of occurrence of hole type defects in the rear surface as well as in the front surface of the slab, as illustrated in FIG. 6. In such a way, the meniscus flow pattern is matched with presence or not of slab defects, defect aspects and causes of a slab produced therewith and stored in the data storage unit 400.

The slab quality predicting unit 500 compares a current meniscus flow pattern in the mold 100 and data of a meniscus flow pattern stored in the data storage unit 400, and extracts slab quality data according to a matched meniscus flow pattern. In other words, the slab quality predicting unit 400 having received the current meniscus flow pattern in the mold 100, which is detected by the meniscus flow detecting unit 300, compares with data of the meniscus flow pattern stored in the data storage unit 400 to detect a matched meniscus flow pattern, and extracts consequent slab quality data. Accordingly, the current meniscus flow pattern of the mold 100 is compared and quality of a slab produced accordingly may be predicted. In addition, the quality data extracted in this way is displayed on the display unit 600.

The display unit 600 displays data provided from any one selected from the meniscus height detecting unit 200, the meniscus flow detecting unit 300, and the meniscus slab quality predicting unit 500, to deliver the data to the user. The display unit 600 may include a display device in various types capable of displaying data. For example, a mobile device as well as a monitor may be included. At this point, information displayed on the display unit 600 may include at least one selected from current temperatures at a plurality of regions in the mold 100, which are measured by the meniscus height detecting unit 200, for example, the plurality of thermocouples, a 3D image and a 2D pattern of the current meniscus flow in the mold 100, which are measured by the meniscus flow detecting unit 300, slab quality and slab defect cause provided from the data storage unit 400, and alarm on normality or defect of the current meniscus flow pattern in the mold 100, as illustrated in FIG. 7.

As described above, the slab quality predicting device according to an embodiment of the present invention detects the meniscus height change in the mold 100 using the meniscus height detecting unit 200, and visualizes the 3D image and 2D pattern using the meniscus flow detecting unit 300 according to the meniscus flow. In addition, defect presence or not of a slab produced with various meniscus flow patterns is tracked and stored in the data storage unit 400. In addition, slab quality according to the current meniscus flow pattern in the mold 100 is extracted from the data storage unit 400, and predicted by the slab quality predicting unit 500 to be displayed on the display unit 600. Accordingly, the meniscus flow pattern may be detected in real time, presence or not of slab defects may also be predicted together to prevent the slab defects in advance, and accordingly productivity may be improved.

Figure 8:
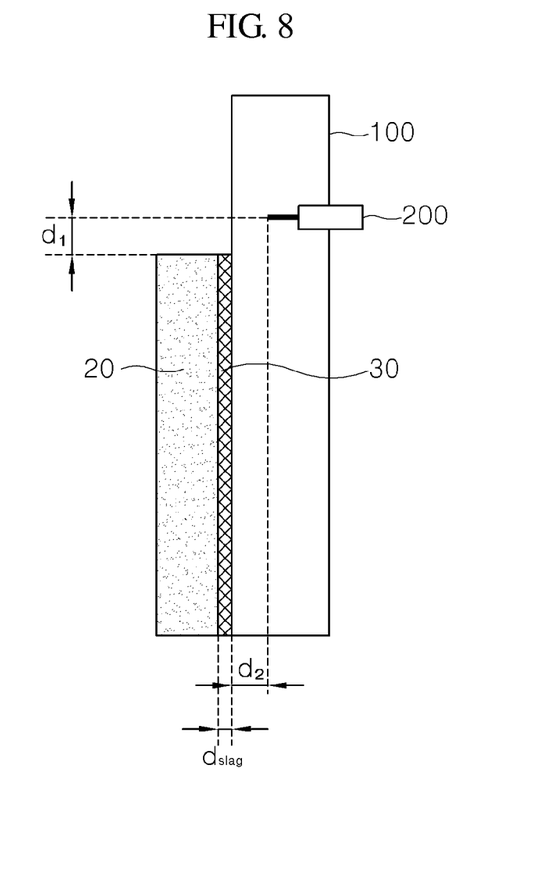
FIG. 8 is a schematic cross-sectional view of a mold according to an embodiment of the present invention.

Furthermore, in the embodiment of the present invention, the meniscus flow detecting unit 300 creates a 3D image and a 2D pattern using temperature differences measured by the plurality of meniscus height detecting units 200, for example, through a plurality of temperature detecting means. However, the 3D image is created by applying the temperatures detected through the temperature detecting means to the following Equation (1) and detecting heights of the meniscus, and the 2D pattern is created therefrom. FIG. 8 is a cross-sectional schematic diagram of the mold 100 illustrated for explaining the following Equation (1).

$$\alpha \times 2.5 \times Q = \left(\frac{K_{slag}}{d_{slag}} + \frac{K_{cu}}{d_{cu}}\right) \times (T_{steel} - T_1) \quad (1)$$

$$d_{cu} = \sqrt{d_1^2 + d_2^2}$$

where $\alpha$ denotes a correction coefficient using an eddy current sensor, Q denotes a real time heat flux using a temperature difference at an input/output side of the mold 100, $K_{slag}$ denotes a heat transfer coefficient of a slag 30, $K_{cu}$ denotes a heat transfer coefficient of the mold 100, $d_{slag}$ denotes the thickness of a slag layer 30, $d_{cu}$ denotes a diagonal distance between the molten steel 20 contacting the short side of the mold 100 and the thermocouple 200, $T_{steel}$ denotes a real time temperature of the molten steel 20, $T_1$ denotes a real time temperature of the thermocouple 200, $d_1$ denotes a vertical distance between the thermocouple 200 and the meniscus, and $d_2$ denotes a distance between a side surface of the mold 100 and a tip of the thermocouple 200. Accordingly, the meniscus height may be detected by calculating the vertical distance d1 between the thermocouple and the meniscus.

In addition, even though a case is described where a plurality of thermocouples are installed between the long sides 110*a* and 110*b* and the short sides 120*a* and 120*b* as the meniscus height detecting unit 200 and used for measuring a meniscus temperature, detection of the heights of the meniscus at the plurality of regions is not limited to measuring the temperature but may be achieved by using induced current, radiation, or the like. For example, an electromagnetic induction sensor, a radiation generator and a measurer, and a thermocouple installed in a refractory thermo-well may be used. The electromagnetic induction sensor may measure the height of the molten steel by measuring a varying induced current, when close to the molten steel. To this end, a plurality of electromagnetic induction sensors are installed at the same height of the long sides and the short sides of the mold 100 to measure the meniscus height at the plurality of regions and visualize the shape thereof. In addition, when the molten steel height is measured by using radiation transmission, and cobalt (Co) 60 may be used as a radiation material. To this end, a radiation generator is installed at one long side of the mold 100 and a radiation measurer may be installed at the other long side. In addition, a thermocouple may be installed in the refractory thermo-well to measure the molten steel temperature. Such a refractory thermo-well thermocouple may be directly installed in width and thickness directions on the meniscus in plurality to measure the meniscus temperature, and measure the meniscus height using a difference in temperature.

Figure 9:
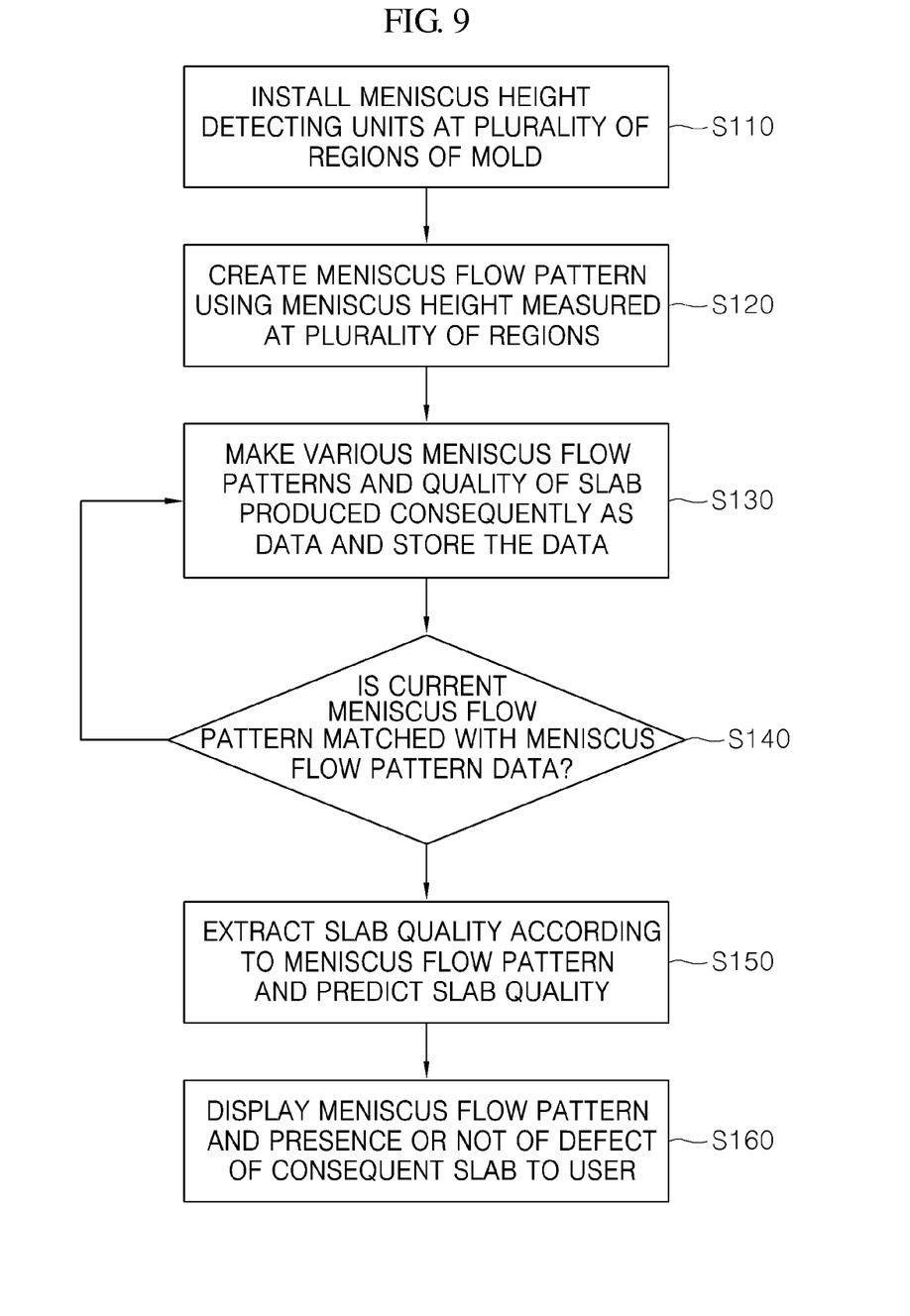
FIG. 9 is a flowchart of a slab quality predicting method according to an embodiment of the present invention.

Description will be provided about a slab quality predicting method using the slab quality predicting apparatus according to the embodiment of the present invention with reference to FIG. 9. FIG. 9 is a flow chart of a process for explaining a slab quality predicting method according to an embodiment of the present invention.

Referring to FIG. 9, a slab quality predicting method according to an embodiment of the present invention includes a step (S110) of installing a plurality of meniscus height detecting units 200 on a plurality of region of the mold 100, a step (S120) of creating a meniscus flow pattern by the meniscus flow detecting unit 300 using the meniscus heights of the plurality of regions, which are detected by the plurality of meniscus height detecting units 200, a step (S130) of making various meniscus flow patterns as data, making slab quality such as presence or not of defects and defect positions of a slab produced accordingly as data, and storing the data in the data storage unit 400, a step (S140) of detecting, by the data storage unit 400, meniscus flow pattern data matched with a current meniscus flow pattern of the mold 100 detected by the meniscus flow detecting unit 300, a step (S150) of, when the current meniscus flow pattern is matched with the meniscus flow pattern data stored in the data storage unit 400, extracting consequent slab quality from the data storage unit 400 to predict the slab quality, and a step (S160) of displaying the meniscus flow pattern and presence or not of consequent slab defects to the user. In addition, when the current meniscus flow pattern is not matched with the meniscus flow pattern stored in the data storage unit 400, the current meniscus flow pattern and quality of the consequent slab are tracked and data thereof is stored in the data storage unit 400 to continuously update the data storage unit 400.

Step S110: A plurality of meniscus height detecting units 200 are installed at the top side of the mold 100 to detect height changes at a plurality of regions of the meniscus in the mold 100. The meniscus height detecting units 200 may use various tools for measuring a temperature, an electromagnetic induction current, radiation, or the like, from which the meniscus height may be measured. In other words, the meniscus height detecting units 200 may use at least any one selected from thermocouples, electromagnetic induction coils, radiation generators and measurers, thermocouples inserted in a refractory thermo-well. For example, a plurality of thermocouples may be prepared in a uniform interval at an identical height of the long and short sides of the mold 100, and an electromagnetic induction sensor may be installed together with the plurality of thermocouples. At this point, the electromagnetic induction sensor may be installed at a central part of the meniscus in plurality. Furthermore, the thermocouples as the meniscus height detecting units 200 may be installed at a height of 10 mm or lower from the meniscus, and preferably, at a height in a range of 4 mm to 9 mm from the meniscus.

Step S120: The meniscus flow detecting unit 300 detects the meniscus flow using the meniscus heights at the plurality of regions detected by the meniscus height detecting unit 200. The meniscus flow detecting unit 300 creates a 3D image according to the meniscus heights and a 2D pattern. For example, the meniscus flow pattern may be displayed in different colors and heights according to temperatures measured by the plurality of thermocouples, and visualized in the 3D image to detect the shape of the entire meniscus. In addition, the 2D pattern may be derived by simplifying the 3D image. For example, when the meniscus height rises due to fluctuation of the molten steel and the meniscus is close to the thermocouples, the temperatures of the thermocouples rise, and when the meniscus height gets lowered and the meniscus is far away from the thermocouples, the temperatures of the thermocouples get lowered. Accordingly, the meniscus flow may be detected using temperatures measured by the plurality of thermocouples and embodied as a predetermined pattern.

Step S130: Slabs produced according to various meniscus flow patterns are tracked and slab quality data such as presence or not of defects, defect positions and defect causes of corresponding slabs are stored in the data storage unit 400. At this point, the data storage unit 400 may store various meniscus flow patterns matched with consequent slab quality. In addition, a cause of slab defect occurrence, namely, a cause of an abnormal meniscus flow pattern or the like may be stored in the data storage unit 400. S140: After a current meniscus flow pattern according to a meniscus height change of the molten steel in the mold 100 is detected through the meniscus height detecting units 200 and the meniscus flow detecting unit 300, meniscus flow pattern data matched with the current meniscus flow pattern is detected from the data storage unit 400. However, when the current meniscus flow pattern is a new meniscus flow pattern that is not stored in the data storage unit 400, the current flow pattern and consequent slab quality data are stored in the data storage unit 400. In other words, every time a new meniscus flow pattern is created which is not stored in the data storage unit 400, the new meniscus flow pattern and consequent slab quality are continuously stored.

Steps S150 and S160: when the current meniscus flow pattern is matched with the meniscus flow pattern data stored in the data storage unit 400, consequent slab quality data is extracted from the data storage unit 400 to predict the slab quality, and the result is displayed to the user through the display unit 600. At this point, information displayed on the display unit 600 includes the 3D image and 2D image of the meniscus flow pattern, quality and a defect image of a consequent corresponding slab, and normality or abnormality of the slab.

Furthermore, in the above-described slab quality predicting method, after the meniscus flow pattern is created, various meniscus flow patterns and consequent slab quality are made as data and stored. However, various meniscus flow patterns and consequent slab quality are made as data and then the current meniscus flow pattern of the mold 100 may be created and compared with pre-stored meniscus flow pattern data. In addition, in an embodiment of the present invention, when a slab defect is predicted to occur from the meniscus flow pattern, it may be controlled to prevent the slab defect from occurring. For example, when the meniscus flow in the mold 100 becomes a bias flow in which intensity differs around the submerged entry nozzle 10, since a meniscus height difference between the short side portions occurs and accordingly a possibility of slab defect occurrence is high, a corresponding slab may be processed in advance with scalfing or the like.

Although the technical idea of the present invention has been described with reference to the specific embodiments, it is for description only and not intended to limit thereto. Therefore, it will be readily understood by those skilled in the art that various modifications and changes can be made thereto without departing from the spirit and scope of the present invention defined by the appended claims.

What is claimed is:

1. An apparatus for predicting slab quality comprising:
a plurality of temperature sensors located in a plurality of regions around a top side of a mold receiving molten steel at a height corresponding to a height of a meniscus of the molten steel in the mold, and detecting a meniscus temperature of the molten steel;
a meniscus flow detecting unit creating a meniscus flow pattern using the meniscus temperatures at the plurality of regions, which are detected by the plurality of temperature sensors;
a data storage unit storing the meniscus flow pattern and quality data of a plurality of slabs produced accordingly;
a slab quality predicting unit predicting the slab quality of an individual slab by comparing the meniscus flow pattern created by the meniscus flow detecting unit for the individual slab to the stored meniscus flow pattern and quality data;
wherein the meniscus flow detecting unit creates a 3-dimensional (3D) meniscus flow image according to the meniscus temperatures and a 2-dimensional (2D) meniscus flow pattern from the 3D image; and
the 3D meniscus flow image is created based on a vertical distance between each temperature sensor and the meniscus, which is calculated by applying the temperatures measured by each temperature sensor to the following Equation (1), $$\alpha \times 2.5 \times Q = \left(\frac{K_{slag}}{d_{slag}} + \frac{K_{cu}}{d_{cu}}\right) \times (T_{steel} - T_1) \quad (1)$$

$$d_{cu} = \sqrt{d_1^2 + d_2^2}$$

where $\alpha$ denotes a correction coefficient using an eddy current sensor, Q denotes a real time heat flux using a temperature difference at an input/output side of the mold, $K_{slag}$ denotes a heat transfer coefficient of a slag, $K_{cu}$ denotes a heat transfer coefficient of the mold, $d_{slag}$ denotes the thickness of a slag layer, $d_{cu}$ denotes a diagonal distance between the molten steel contacting a short side of the mold and the temperature sensor, $T_{steel}$ denotes a real time temperature of the molten steel, $T_1$ denotes a real time temperature of the temperature sensor, $d_1$ denotes a vertical distance between the temperature sensor and the meniscus, and $d_2$ denotes a distance between a side surface of the mold and a tip of the temperature sensor.

2. The apparatus of claim 1, further comprising a display unit displaying the meniscus flow pattern and the consequent slab quality to a user.

3. The apparatus of claim 1, wherein the temperature sensors are installed at an identical height on the top side of the mold.

4. The apparatus of claim 3, wherein the temperature sensors are installed at a height in a range of 4.5 mm to 9.5 mm from the meniscus.

5. The apparatus of claim 1, wherein the 3D meniscus flow image is created using temperature differences between the plurality of regions measured through the temperature detecting means.

6. The apparatus of claim 1, wherein after provision of the molten steel to the mold is completed, the meniscus flow pattern is created at least once.

7. The apparatus of claim 1, wherein the data storage unit performs matching of the meniscus flow pattern with at least one selected from presence or not of defects, defect positions, and defect shapes of the consequent slab and stores the matched results.

8. The apparatus of claim 1, wherein the display unit displays at least any one piece of information provided from the temperature sensors, the meniscus flow detecting unit, the data storage unit, and the slab quality predicting unit.

9. A method of predicting slab quality comprising:
installing a plurality of temperature sensors in a plurality of regions around a top side of a mold receiving molten steel at a height corresponding to a height of a meniscus of the molten steel in the mold, and detecting a meniscus temperature of the molten steel;
creating a meniscus flow pattern using the meniscus temperatures at the plurality of regions, which are detected by the plurality of temperature sensors;
comparing pre-stored meniscus flow pattern data with a current meniscus flow pattern in the mold; and
predicting the slab quality of the slab associated with the current meniscus flow pattern based on the comparison,
wherein creating the meniscus flow pattern includes creating a 3-dimensional (3D) meniscus flow image according to the meniscus temperatures and a 2-dimensional (2D) meniscus flow pattern from the 3D image, and
the 3D meniscus flow image is created based on a vertical distance between each temperature sensor and the meniscus, which is calculated by applying the temperatures measured by each temperature sensor to the following Equation (1), $$\alpha \times 2.5 \times Q = \left(\frac{K_{slag}}{d_{slag}} + \frac{K_{cu}}{d_{cu}}\right) \times (T_{steel} - T_1) \quad (1)$$

$$d_{cu} = \sqrt{d_1^2 + d_2^2}$$

where $\alpha$ denotes a correction coefficient using an eddy current sensor, Q denotes a real time heat flux using a temperature difference at an input/output side of the mold, $K_{slag}$ denotes a heat transfer coefficient of a slag, $K_{cu}$ denotes a heat transfer coefficient of the mold, $d_{slag}$ denotes the thickness of a slag layer, $d_{cu}$ denotes a diagonal distance between the molten steel contacting a short side of the mold and the temperature sensor, $T_{steel}$ denotes a real time temperature of the molten steel, $T_1$ denotes a real time temperature of the temperature sensor, $d_1$ denotes a vertical distance between the temperature sensor and the meniscus, and $d_2$ denotes a distance between a side surface of the mold and a tip of the temperature sensor.

10. The method of claim 9, further comprising storing a plurality of meniscus flow pattern data and a plurality of slab quality data accordingly produced.

11. The method of claim 10, further comprising displaying the meniscus flow pattern and the consequent slab quality to a user.

12. The method of claim 10, further comprising, when the current meniscus flow pattern is not matched with the meniscus flow pattern data, making the current meniscus flow pattern and the consequent slab quality as data and storing the data.

* * * * *